(12) United States Patent
Stratis et al.

(10) Patent No.: US 10,703,532 B2
(45) Date of Patent: Jul. 7, 2020

(54) SYSTEM FOR COMPOUNDING AND PACKAGING READY TO RECONSTITUTE OPHTHALMIC DRUG POWDERS TO A SOLUTION OR TO A SUSPENSION FOR ADMINISTRATION TO AN EYE OF A PATIENT

(71) Applicant: ARCHON PHARMACEUTICAL CONSULTING LLC, Wilmington, DE (US)

(72) Inventors: William Stratis, Brooklyn, NY (US); Serafin Gonzalez, Miami, FL (US)

(73) Assignee: ARCHON PHARMACEUTICAL CONSULTING LLC, Wilmington, DE (US)

( * ) Notice: Subject to any disclaimer, the term of this patent is extended or adjusted under 35 U.S.C. 154(b) by 379 days.

(21) Appl. No.: 15/725,892

(22) Filed: Oct. 5, 2017

(65) Prior Publication Data
US 2018/0086499 A1    Mar. 29, 2018

Related U.S. Application Data

(60) Continuation of application No. 15/604,429, filed on May 24, 2017, which is a division of application No.
(Continued)

(51) Int. Cl.
*A61J 1/14*    (2006.01)
*A61J 1/06*    (2006.01)
(Continued)

(52) U.S. Cl.
CPC ............ *B65D 17/06* (2013.01); *A61F 9/0008* (2013.01); *A61J 1/1418* (2015.05); *A61J 1/1481* (2015.05);
(Continued)

(58) Field of Classification Search
CPC ..... A61F 9/0008; A61F 9/0026; A61J 1/1412; A61J 1/1418; A61J 1/1475; A61J 1/1487;
(Continued)

(56) References Cited

U.S. PATENT DOCUMENTS 2,999,943 A    9/1961  Willard
3,410,444 A    11/1968 Morane
(Continued)

FOREIGN PATENT DOCUMENTS

DE    202004009453    8/2004
WO    WO 2006/076492    6/2006

OTHER PUBLICATIONS

International Search Report and Written Opinion dated Jan. 29, 2014 for PCT/US2013/055153.
(Continued)

*Primary Examiner* — Adam Marcetich
(74) *Attorney, Agent, or Firm* — Leason Ellis LLP

(57) ABSTRACT

A system and method for mixing compounds is disclosed. Accordingly to one embodiment a transfer device is provided that allows for diluent from a syringe to be introduced into a container having a first compound (e.g., powder) in a sterile manner. In second and third embodiments, systems are shown for combining and mixing first and second compounds contained in first and second containers in a sterile manner. Various dropper tips for dispensing the mixed compounds are disclosed.

21 Claims, 6 Drawing Sheets

Related U.S. Application Data

14/357,728, filed as application No. PCT/US2013/055153 on Aug. 15, 2013, now Pat. No. 9,688,434.

(60) Provisional application No. 61/792,792, filed on Mar. 15, 2013, provisional application No. 61/738,535, filed on Dec. 18, 2012, provisional application No. 61/684,467, filed on Aug. 17, 2012.

(51) Int. Cl.
| | |
|---|---|
| *A61J 1/20* | (2006.01) |
| *A61F 9/00* | (2006.01) |
| *B65D 17/00* | (2006.01) |
| *B65D 47/18* | (2006.01) |

(52) U.S. Cl.
CPC ............ *A61J 1/067* (2013.01); *A61J 1/20* (2013.01); *A61J 1/2075* (2015.05); *A61J 1/2089* (2013.01); *A61J 1/2096* (2013.01); *B65D 47/18* (2013.01); *Y10S 215/08* (2013.01); *Y10S 604/905* (2013.01)

(58) Field of Classification Search
CPC .. A61J 1/20; A61J 1/2006; A61J 1/201; A61J 1/2013; A61J 1/2024; A61J 1/2027; A61J 1/2068; A61J 1/2075; A61J 1/067; B65D 17/06; B65D 47/122; B65D 47/123; B65D 47/14; B65D 47/141; B65D 47/142; B65D 47/143; B65D 47/145; B65D 47/146; B65D 1/0246; B65D 45/30; B65D 45/305; B65D 45/325
See application file for complete search history.

(56) References Cited

U.S. PATENT DOCUMENTS

| | | | |
|---|---|---|---|
| 3,677,248 A | 7/1972 | McPhee | |
| 3,802,604 A | 4/1974 | Morane et al. | |
| 3,857,423 A | 12/1974 | Ronca, Jr. | |
| 3,917,063 A | 11/1975 | Chibret et al. | |
| RE29,656 E | 6/1978 | Chittenden et al. | |
| 4,201,208 A | 5/1980 | Cambio, Jr. | |
| 4,227,615 A * | 10/1980 | Flick | B65D 25/54 200/82 R |
| 4,336,802 A | 6/1982 | Stone et al. | |
| 4,384,960 A | 5/1983 | Polley | |
| 4,573,506 A | 3/1986 | Paoletti | |
| 4,591,357 A | 5/1986 | Sneider | |
| 4,986,322 A | 1/1991 | Chibret et al. | |
| 5,105,993 A * | 4/1992 | La Haye | A61F 9/0008 210/321.89 |
| 5,156,284 A | 10/1992 | del Pilar Pia Rodriguez | |
| 5,409,141 A | 4/1995 | Kikuchi et al. | |
| 5,462,101 A * | 10/1995 | Mouchmouchian | A61J 7/0023 141/18 |
| 5,573,525 A | 11/1996 | Watson | |
| 5,634,714 A | 6/1997 | Guild | |
| 5,740,654 A * | 4/1998 | Manni | A61J 1/2089 141/329 |
| 5,778,902 A | 7/1998 | Nagy | |
| 5,865,309 A | 2/1999 | Futagawa et al. | |
| 6,179,125 B1 * | 1/2001 | Kvitrud | B65D 1/02 206/459.1 |
| 6,457,899 B1 | 10/2002 | Lin | |
| 7,210,575 B2 | 5/2007 | Oswald | |
| 7,308,915 B2 | 12/2007 | Johns et al. | |
| 7,861,855 B2 | 1/2011 | Casey | |
| 8,075,545 B2 | 12/2011 | Moy et al. | |
| 8,147,477 B2 | 4/2012 | Smith et al. | |
| 2002/0104766 A1 | 8/2002 | De Laforcade | |
| 2002/0115980 A1 | 8/2002 | Niedospial, Jr. | |
| 2003/0030278 A1 * | 2/2003 | Shimei | A61J 1/2089 285/331 |
| 2003/0088232 A1 | 5/2003 | Duell | |
| 2003/0159983 A1 | 8/2003 | Naji | |
| 2004/0065635 A1 | 4/2004 | Turnbough | |
| 2004/0134562 A1 | 7/2004 | Engel | |
| 2004/0249341 A1 | 12/2004 | Newbrough et al. | |
| 2005/0033260 A1 | 2/2005 | Kubo et al. | |
| 2005/0184091 A1 | 8/2005 | Abergel | |
| 2005/0252879 A1 | 11/2005 | Pedmo | |
| 2006/0106360 A1 | 5/2006 | Wong | |
| 2006/0289316 A1 | 12/2006 | Henry | |
| 2007/0079894 A1 | 4/2007 | Kraus | |
| 2007/0093765 A1 | 4/2007 | Kawashiro | |
| 2007/0095721 A1 * | 5/2007 | Davis | B65D 23/085 206/581 |
| 2007/0233020 A1 * | 10/2007 | Hearne | A61F 9/0008 604/295 |
| 2008/0015539 A1 | 1/2008 | Pieroni et al. | |
| 2008/0172024 A1 | 7/2008 | Yow | |
| 2008/0245314 A1 | 10/2008 | Brodowski et al. | |
| 2008/0245380 A1 | 10/2008 | Ecker et al. | |
| 2009/0152302 A1 | 6/2009 | Grevin | |
| 2009/0274762 A1 | 11/2009 | Willis | |
| 2009/0326506 A1 | 12/2009 | Hasegawa | |
| 2010/0016826 A1 | 1/2010 | Billiet-Prades et al. | |
| 2010/0022986 A1 | 1/2010 | Breuer-Thal et al. | |
| 2010/0063473 A1 | 3/2010 | Schwarz | |
| 2010/0198147 A1 | 8/2010 | Perovitch | |
| 2011/0022023 A1 | 1/2011 | Weitzel | |
| 2011/0042255 A1 * | 2/2011 | Traboulsi | B65D 23/00 206/459.5 |
| 2011/0042944 A1 | 2/2011 | Johns et al. | |
| 2011/0087164 A1 | 4/2011 | Mosler | |
| 2011/0218511 A1 | 9/2011 | Yokoyama | |
| 2011/0264069 A1 * | 10/2011 | Bochenko | A61J 1/2096 604/404 |
| 2012/0031401 A1 * | 2/2012 | Berger | A61M 15/08 128/203.12 |
| 2012/0067429 A1 | 3/2012 | Mosler et al. | |
| 2012/0172830 A1 * | 7/2012 | Yokoyama | A61J 1/2089 604/413 |
| 2012/0220949 A1 | 8/2012 | Davies | |
| 2012/0234432 A1 | 9/2012 | Lamboux | |
| 2012/0323210 A1 * | 12/2012 | Lev | A61J 1/2089 604/405 |
| 2013/0220484 A1 | 8/2013 | De Marco | |
| 2013/0245579 A1 | 9/2013 | Kouyoumjian et al. | |
| 2014/0039413 A1 * | 2/2014 | Jugl | A61M 5/346 604/240 |

OTHER PUBLICATIONS

Non-Final Office Action in corresponding U.S. Appl. No. 14/357,728, dated May 13, 2016.

Final Office Action in corresponding U.S. Appl. No. 14/357,728, dated Nov. 1, 2016.

* cited by examiner

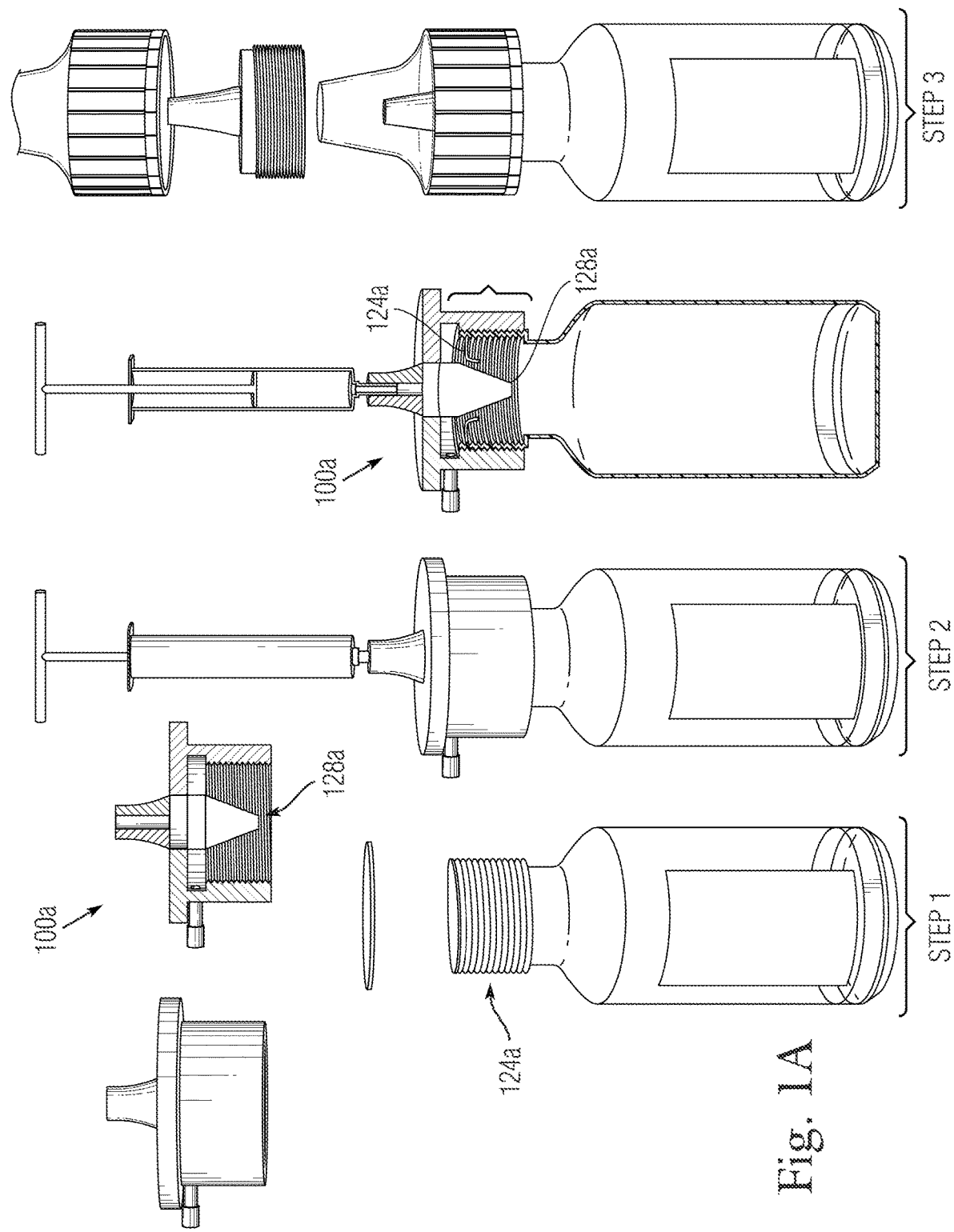

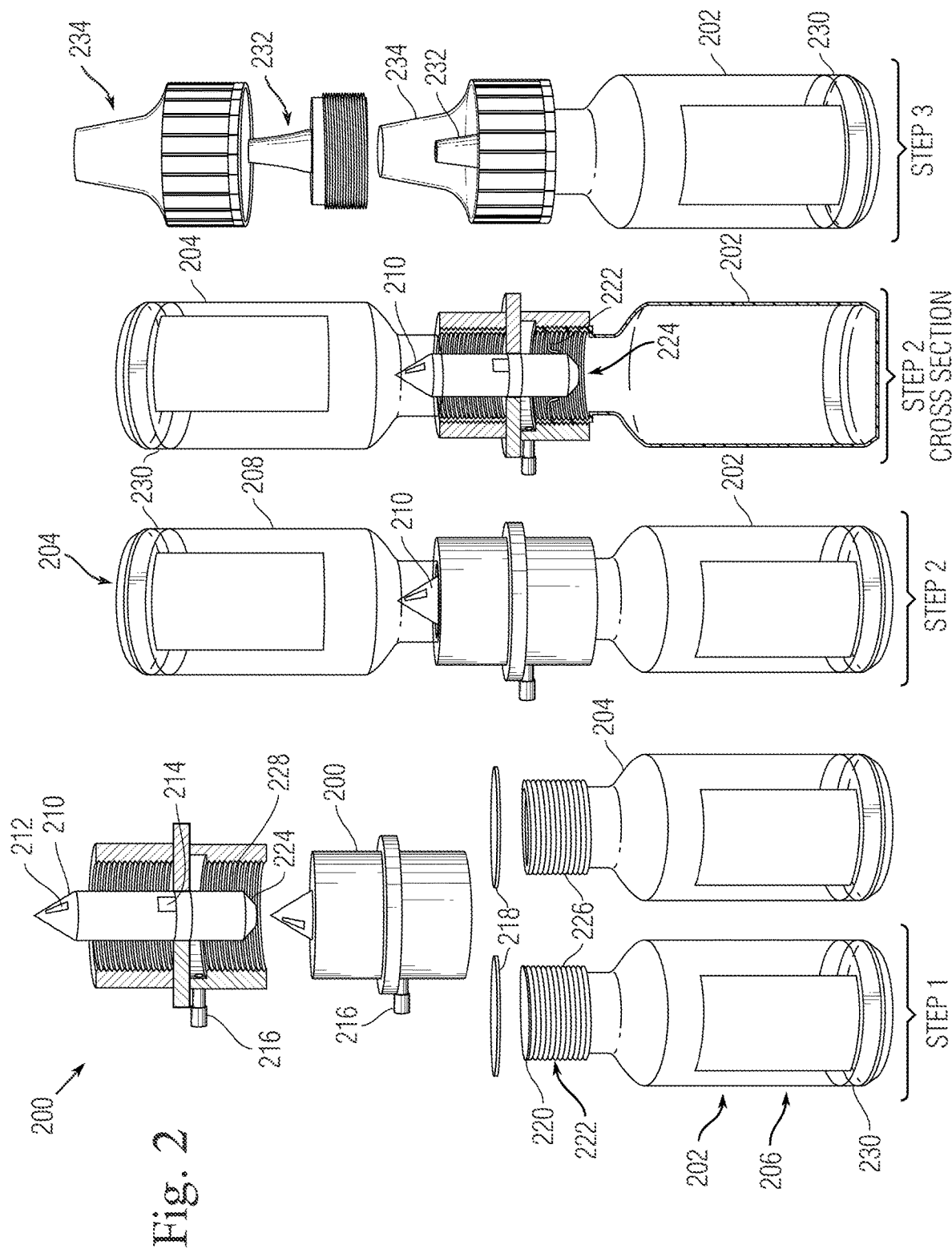

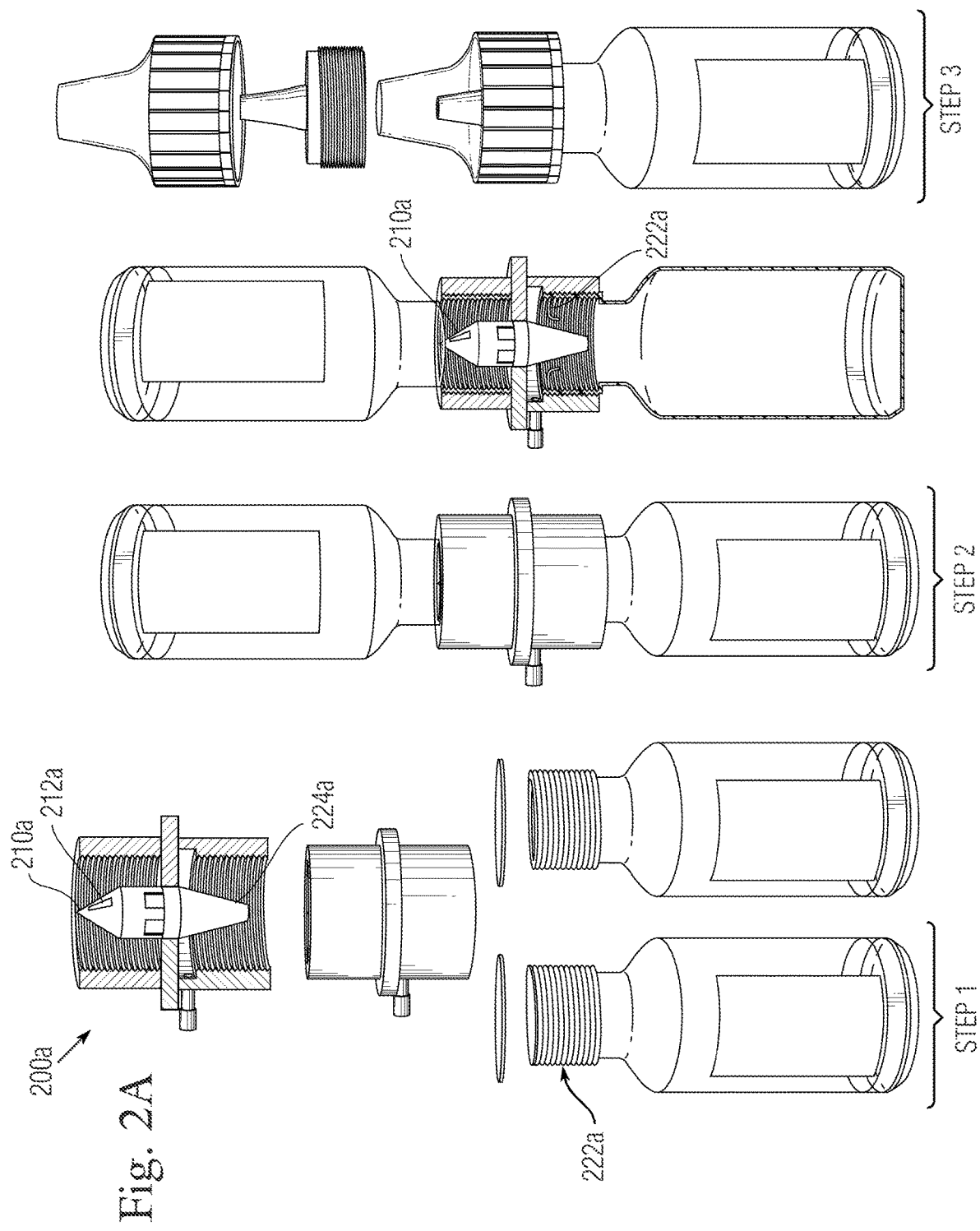

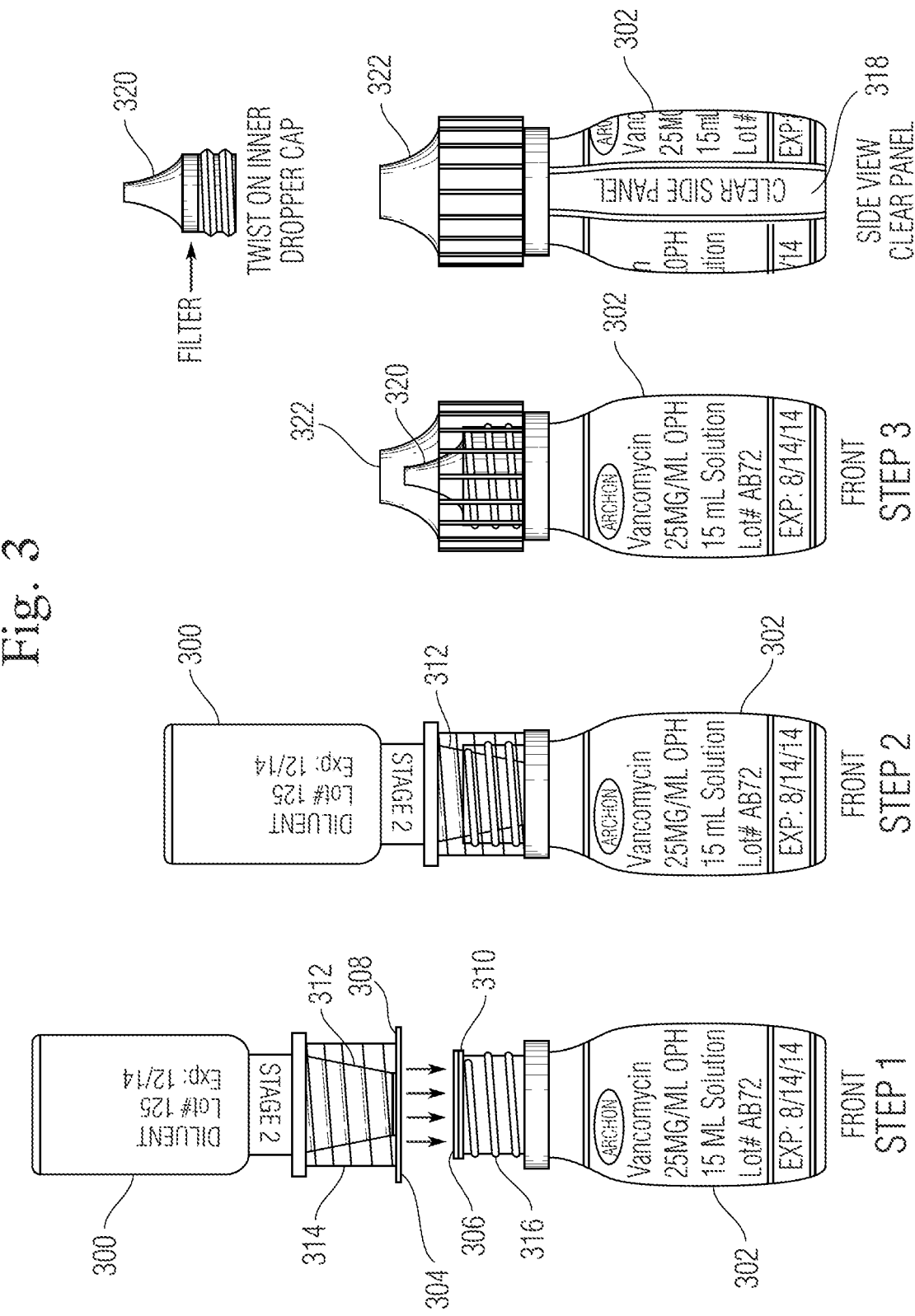

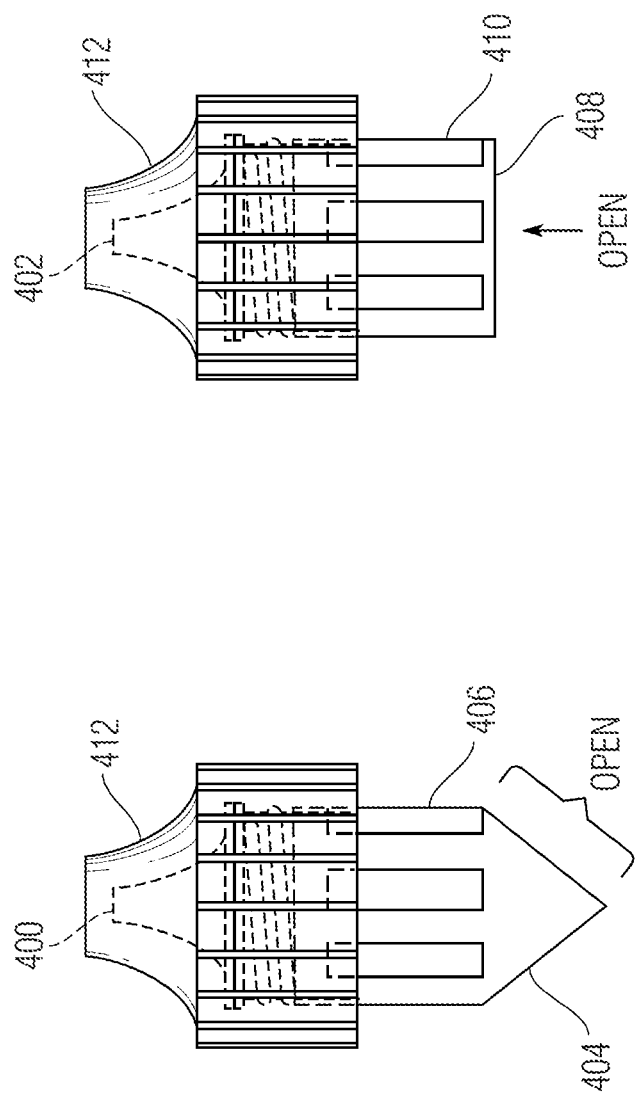

SYSTEM FOR COMPOUNDING AND PACKAGING READY TO RECONSTITUTE OPHTHALMIC DRUG POWDERS TO A SOLUTION OR TO A SUSPENSION FOR ADMINISTRATION TO AN EYE OF A PATIENT

CROSS REFERENCE TO RELATED APPLICATION

This application is a continuation application of U.S. application Ser. No. 15/604,429 filed May 24, 2017, which is a divisional application of U.S. application Ser. No. 14/357,728, filed May 12, 2014, which is a national stage application under 35 U.S.C. § 371, of PCT Application No. PCT/US2013/055153, filed on Aug. 15, 2013, which claims the benefit of priority under 35 U.S.C. Section 119(c) of U.S. Application Ser. No. 61/684,467, filed on Aug. 17, 2012, U.S. Application Ser. No. 61/738,535, filed Dec. 18, 2012, and U.S. Application Ser. No. 61/792,792, filed Mar. 15, 2013 and the entire disclosures of each of the above identified applications are incorporated herein by reference in their entireties.

BACKGROUND

There is an unmet need for the development of a closed environment for pharmaceutical formulation that will allow healthcare professionals to easily compound and dispense therapeutically valuable and medically necessary medications, that are commercially unavailable due to relatively short drug stability, stringent compounding/manufacturing requirements and/or lack of proper facilities for sterile preparation of pharmaceutical products, from powder to a solution/suspension form.

One ophthalmic mixing system that currently exists includes an open environment transfer of liquid diluents to an open environment glass bottle with powder that is mixed and then closed with a glass ophthalmic bottle dropper tip with rubber or silicone bulb. This product is available as Phospholine Iodide® (echothiophate) from Wyeth-Ayerst. It is referred to as an open system because it does not contain any features to prevent the contamination of the product during mixing and use or to protect the compounder from exposure to the product.

SUMMARY

A new and unique system for compounding, labeling, and dispensing "Ready to Reconstitute Drug Powders or Solutions to Solution or to a Suspension or to an injectable". In specific embodiment, the system can be used as an ophthalmic drop delivery container.

In one embodiment, described herein is a Compounding System which makes the availability of once unstable or non-mixable medications with short stability dating available to patients worldwide (especially where no specialty sterile compounding or manufacturing facilities are available for the preparation of such medications) for multiple medical indications. In one embodiment, the system is an Ophthalmic Medication. In one embodiment, the system is for treatment of multiple ophthalmic indications.

The system allows a health care professional or patient to reconstitute powder or solution with a system that locks together when transferring diluents solutions to powders or solution a closed environment.

A unique locking and vented diluent transferring device that screws onto a drug containing bottle with powder minimizes the risk of medication contamination or the inhalation of aerosolized powders upon diluent transfer present in other mixing systems. In one embodiment, the bottle is a bottle for dispensing an ophthalmic drug.

A unique conical design of the diluent solution neck/transfer chamber permits the solution to be transferred centrally which minimizes run off and spillage when opening.

The sterile easy to screw on dropper tip and outer cap (which all interlock with the assistance of a locking/dimple/nipple) can be easily connected to the reconstitution bottle after opening the sterile packet that houses both items.

Clear side or bottom panel permits viewing of solution to ensure it mixed properly (no visible signs of incompatibility such as clumping or precipitation) and permits patient to observe remaining volume as it is used.

In one embodiment, the bottle is adapted with a dropper. In one embodiment, the drug is contained in Ophthalmic bottles. Ophthalmic bottles are available in clear, opaque, or amber colored combinations to address potential drug/light sensitivity issues.

Sterile gloves can be provided for use by the compounder for added protection of both the compounded medication and as personal protective equipment for the compounder from topical exposure to the medication.

Sterile 70% Isopropyl Alcohol pads are provided for additional disinfection at the point of connection between the syringe and the transfer device and between the transfer device and the drug bottle. In a specific embodiment, the bottle is an ophthalmic bottle.

Beyond-use date/Discard after date stickers can be provided for placement onto the final bottle product that has been prepared for use by the patient. In one embodiment, the bottle is an ophthalmic bottle.

BRIEF DESCRIPTION OF THE DRAWINGS

The novel features that are characteristic of the present disclosure are explained in the DETAILED DESCRIPTION OF THE PREFERRED EMBODIMENTS Section. The preferred embodiments are best understood by referencing the following detailed descriptions in connection with the accompanying drawings in which:

FIG. 1a is a front view of a fluid transfer system in various stages of use according to an embodiment of the invention;

FIG. 2 is a front view of a fluid transfer system in various stages of use according to another embodiment of the invention;

FIG. 2a is a front view of a fluid transfer system in various stages of use according to another embodiment of the invention;

FIG. 3 is a front view of a fluid transfer system in various stages of use according to a further embodiment of the invention.

FIG. 4 is an illustration of two variations of a dropper tip drainage port.

DETAILED DESCRIPTION OF THE PREFERRED EMBODIMENTS

Figure 1:
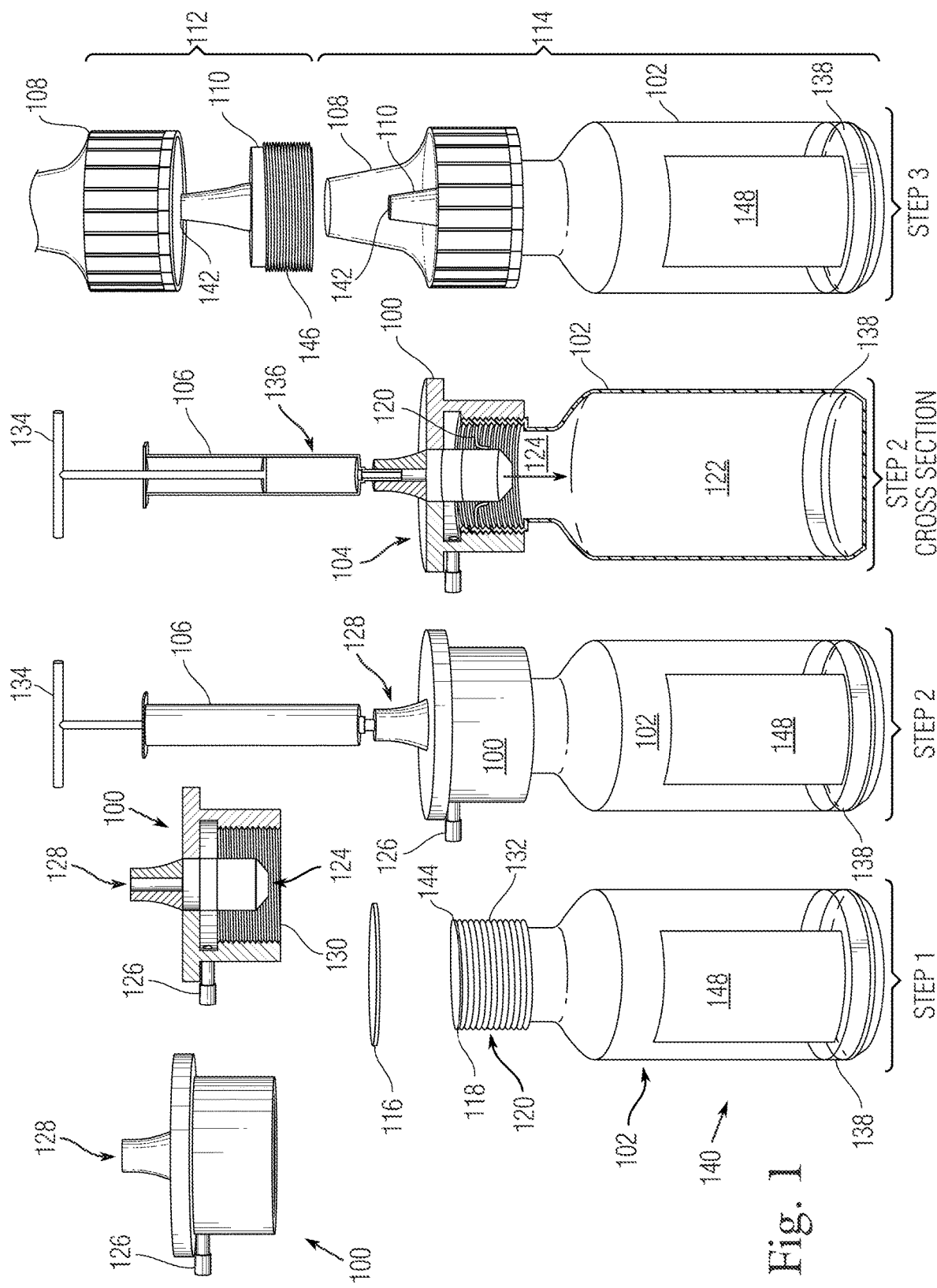
FIG. 1 is a front view of a fluid transfer system in various stages of use according to an embodiment of the invention.

The present invention relates to a closed environment pharmaceutical Compounding System that will allow healthcare professionals to easily compound and dispense therapeutically valuable and medically necessary therapeutics that are commercially unavailable due to short stability dating or unique compounding requirements, from powder or solution to a solution/suspension form. This closed environment will limit the exposure of the drug to microbial or particulate contaminants carried by the environment as well as protect the compounder/healthcare professional from potential topical or inhalation exposure of the medication (using some present compounding methods or devices). In one embodiment, the pharmaceutical system is for the preparation of an ophthalmic Medication.

Referring to FIG. 1, a sterile vented and two-sided luer-lock and threaded twist locking transfer device 100 is shown. The transfer device 100 includes a vent 126, a luer-lock 128, and threads 130 for twisting and locking engagement to a plastic bottle 102, such as an Ophthalmic Bottle, that contains a medication in a powder form 140 that is to be mixed from powder into solution/suspension form as set forth in more detail below. The solution/suspension can be delivery through a dropper, injection, intravenously, or other routes of administration.

FIG. 1 also contains a cross sectional view of the individual pieces (Step 2, Cross Section). Referring to FIG. 1, Step 2 Cross Section, the transfer device 100 is show in partial cross section (104) threaded onto the plastic ophthalmic bottle that contains powder 102. A diluent syringe 106 is shown in cross section connected to the transfer device 100 which is connected to the ophthalmic bottle 102.

Referring to FIG. 1, Step 3, a bottle cap 108 and dropper tip 110 are shown in an exploded configuration at 112 and in a configuration with the bottle cap 108 threaded onto the dropper tip 110 threaded onto the ophthalmic bottle 102 at 114.

Referring to FIG. 1, a cap 116 is shown that is typically provided by the manufacturer. If cap 116 is present, it is removed from the ophthalmic bottle with powder 102.

A primary sterility barrier/aluminum seal barrier 118 is removed to expose the opening of the ophthalmic bottle with powder 102. Once removed the surface and rim of the bottle of which the seal sat on can be cleaned with a sterilizing agent, such as a 70% isopropyl alcohol pads swabbed over the surface, for physical removal of particulates and chemical disinfection.

A secondary sterility barrier 120 of an sterile inert material that will keep the inner mixing chamber 122 of the ophthalmic bottle with powder 102 closed until the membrane 120 is broken by a conical drainage tube 124 of the transfer device 100 when the transfer device 100 is connected to the ophthalmic bottle 102 by turning clockwise until locked by engagement of the threads 130 of the transfer device and the threads 132 of the bottle 102.

As shown in FIG. 1, Step 2, the Diluent Syringe 106 is connected at the luer-lock connection point 128 by gently twisting clockwise until locked in.

Once all three stages have been locked in (i.e., the syringe 106, the transfer device 100, and the bottle 102) with the assistance of the luer-lock connection 128 and the threads of the ophthalmic bottle's neck 132, the syringe arm 134 is slowly pressed down until all the diluent 136 is released and transferred to the bottom of the ophthalmic bottle 102 where it can be seen through the clear panel 138 for mixture viewing by a compounder (user).

While all 3 stages are still connected the user can slowly rotate the three pieces clockwise to swirl the powder and solution until the powder dissolves completely (other acceptable mixing motions can be used, including counter-clockwise motion, so long as care is taken so not as to prematurely disengage the connected pieces).

Once in solution (e.g., the powder and diluent are mixed), the diluent syringe 106 can be removed from the transfer device 100, which can in turn be removed from the ophthalmic bottle 102 and discard.

The sterile dropper tip 110 and bottle cap 108 can be provided in sterile plastic packaging. After the dropper tip 110 and the bottle cap 108 are removed from the sterile packaging they can be attached to the ophthalmic bottle 102 with the newly compounded solution or suspension (combination of powder 140 and diluent 136). Care should be taken to avoid contact between the top edge 144 of the ophthalmic bottle 102 with anything but the dropper tip 110. The dropper tip 110 can be rotated clockwise until the dimple/nipple lock is activated and the dropper tip 110 is locked in engagement with the bottle 102. This step should be performed immediately after the bottle 102 has been separated from the syringe 106 and the transfer device 100 in order to limit exposure of the opened container to particulate matter and microbial organisms that may compromise the sterility of the solution/suspension.

Cap 108 can be placed onto the dropper tip 110 and rotated such that the threads 146 of the dropper tip 110 and the internal threads (not shown) of the cap 108 engage until closed. The locked and complete cap 108, dropper tip 110, and ophthalmic bottle 102 combination can be seen at 114 in FIG. 1. The bottle 102 can include a label 148 that can be used to identify the contents of the bottle and contents can be dispensed through the top 142 of dropper 110.

FIG. 1A shows as system that is similar to the system shown in FIG. 1. As shown in FIG. 1A, a transfer device 100a is provided with a drainage tube 128a that has a more sharply angled shape. A drainage tube having a shape as shown in FIG. 1A is advantageous for piercing membranes 124a because less force will be required to puncture the membrane 124a due to the sharper point shape. In addition, the drainage tube 128a can also be advantageous for piercing thicker and/or reinforced membranes.

FIG. 2 shows a two-sided diluents transferring spike with threaded transfer device 200 that can be used between two ophthalmic bottles, 202 and 204 in which a first ophthalmic bottle 202 contains a drug powder 206 to be mixed and a second bottle 204 containing pre-measured diluent 208 that can be used for compounding the powder to solution/suspension. The transfer device 200 includes a spike 210 that has fluid transfer ports 212 and 214 that allow the diluent solution to flow more easily as well as a vent 216 for preventing negative pressures that can impede the flowing of the diluents from one bottle to another. The transfer device 200 includes at the other end of spike 210 a drainage tube 224.

Referring to FIG. 2, Step 1, once the caps 218 and aluminum seals/foils 220 have been removed (shown in place on bottle 202 and removed from bottle 204), the bottles top surfaces and edges of the two bottles can be disinfected with 70% isopropyl alcohol. The inner sterility membrane 222 of the bottle 202 containing the powder is punctured by the drainage tube 224 of the transfer device 200 to allow the transfer of diluents from one bottle to the other so the powder can be mixed into solution. In one example, this is accomplished by first attaching bottle 204 containing the diluents solution 208 to the vented transfer device 200 and then the bottle 202 containing the powder 206 is carefully twisted onto the vented transfer device 200 using the threaded or beveled edges 226 of the bottles that twists onto the threads 228 of the transfer device 200. After connecting bottles 202 and 204 to the transfer device 200, bottles and transfer device are inverted so that the diluent bottle 204 is on top with respect to the powder containing bottle 202 as shown in FIG. 2, Step 2 and Step 2 Cross Section. In this configuration, the diluent solution, via gravity, passes through the connector spike 210 and the conical drainage tube 224 of the transfer device 200. Bottle 202 and 204 can each include a clear viewing panel 230 that can be used to view the diluent, the powder, and the transfer of the diluent into the powder containing bottle. After the diluent has been transferred to the powder containing bottle and with the two bottles still connected via the transfer device, the assembly can be gently swirled clockwise until the drug is in solution or uniformly mixed in the case of suspensions. Panel 230 of bottle 202 can be used to confirm proper mixing. Finally, as shown in Step 3, the bottle that contained the diluents 204 and the transfer device 200 are separated from bottle 202 and discarded. A dropper tip 232 is twisted on until locked and then the dropper cap 234 is placed onto the tip and turned clockwise until locked.

FIG. 2A shows as system that is similar to the system shown in FIG. 2. As shown in FIG. 2A, a transfer device 200a is provided with a drainage tube 224a that has a more sharply angled shape. A drainage tube having a shape as shown in FIG. 2A is advantageous for piecing membranes 222a because less force will be required to puncture the membrane 222a due to the sharper point shape. In addition, the drainage tube 224a can also be advantageous for piercing thicker and/or reinforced membranes. In addition, spike 210a can be provided with additional fluid transfer ports 214a. These ports help the diluent to drain from the bottle in less time and the location of fluid transfer ports 214a helps ensure that all (or nearly all) of the diluent is drained from the bottle. Moreover, spike 210a is show with a slightly shorter configuration so that the tip of the spike 210a does not extend past the end of transfer device 200a. This configuration in which the spike 210a is more fully shrouded helps prevent inadvertent contact of the spike 210a with contaminants and non-sterile surfaces.

FIG. 3 displays an embodiment of two ophthalmic bottles (one containing a diluent 300 and another containing a powder 302 which will be mixed into solution or into a suspension). The bottle 300, 302 include caps 304, 306 and protective foils 308, 310 that are removed prior to the two bottles being connected together. After the caps and foils are removed, one bottle is twisted onto the opening of the other bottle until both bottles are locked together, as shown in Step 2. One bottle can include internal grooves 314 and the other can include corresponding external grooves 316 that facilitate the twisting engagement between the bottles. A conical transfer tube 312 allows the diluents to drain from one bottle 300 to the bottle containing the powder 302. The contents of the bottle can be viewed through the side or bottom viewing panel 318. The bottles can be swirled clockwise while still connected so that the powder is mixed into solution or suspension. After the mixing, the top bottle 300 that formally contained the diluents can be removed and discard. A dropper tip 320 can twist on to the threads 316 of bottle 302 now containing the powder/diluent mixture by twisting clockwise until locked into place. The dropper tip 320 may or may not contain an additional filter if needed for filtering solution as it is squeezed out by the patient when self-administering the drops (if needed). A traditional snap in tip may also be used however the screw on is preferred for added security. A sterile dropper cap 322 can be screwed onto the dropper tip 320 for easy closing and opening.

FIG. 4 displays an embodiment of different ophthalmic dropper tips 400 and 402 that may be used in the event that the broken internal sterility membrane/barrier (e.g., barrier 120, 222 in FIGS. 1 and 2, respectively) (inside the ophthalmic bottle that contains the powdered solution) decreases or blocks the flow of the solution upon use. The dropper tip 400 includes a spike end 404 that include an open end in fluid communication with draining ports 406. Dropper tip 402 is similar except it includes a relatively flat bottom end 408. Dropper tip 402 includes draining ports 410. Both dropper tips 400 and 402 are configured to be removable engageable with a protective cap 412.

Beyond-use date/discard after date stickers which are provided for placement onto the final ophthalmic bottle that has been prepared for use by the patient have not been displayed in the drawings as they vary in style and color.

This ready-to-mix and dispense medication compounding system provides: a pre-measured sterile diluent in a syringe that luer locks onto a sterile vented transfer device (transfer device contains a vented pin that filters air and other particles while preventing a negative pressure environment that would affect the flow of the diluent solution into the bottle) that twists on with threads and connects onto a plastic bottle with medication in a powder form for mixing. In one embodiment, the medication is an ophthalmic medication.

In another embodiment the vented transfer device may include a separate injection port to permit injecting an additional substance (solution or medication) into the mixing chamber without disconnecting the primary syringe with solution that has been luer locked into the bottle that contains the powder or solution. This cap will likewise be screwed on till locked.

Bottle sizes may vary from 2.5 mL to 30 mL depending on the final volume required.

A primary sterility barrier (aluminum seal under the capped ophthalmic bottle containing the powder as supplied by the manufacturer).

A secondary sterility barrier (internal membrane within the neck of the drug powder bottle) for the protection of the medication while preparing for mixing. This secondary barrier will be made of an inert non-reactive, sterile, material that will maintain its integrity until the drainage cone, upon connection of the transfer device, pierces the center of the membrane thus causing it to snap into two exposing the inner mixing chamber with the powder to the diluents when the syringe is pressed. In an embodiment, the drug is an ophthalmic drug.

A unique conical drainage tube that will minimize spillage and further facilitate the flowing of the diluents towards the powder within the mixing chamber of the bottle. In one embodiment, the bottle is adapted with a dropper. In one embodiment, the bottle is an ophthalmic bottle.

A see through plastic window (include on the side or bottom of the bottle which allows the compounder to look at the solution so it is mixed properly).

In one embodiment, the system also includes a unique threaded sterile dropper tip and cap. In one embodiment, the sterile dropper tip contains a special lock-on dimple/nipple that will protect the dropper tip from being opened and spilling of the drug solution or compromising the sterility of the solution once compounded and dispensed. In one embodiment, the system is for patient drug administration into the eye. A snap-on type tip may also be used however the screw on is preferred for added security and prevention of tampering. The dropper tip will have internal and external threads for twisting onto the ophthalmic bottle and for twisting the cap onto the dropper tip. The sterile dropper cap will then screw onto the dropper tip for easy closing and opening.

Beyond-use/Discard after labels can also be provided to be used on the bottle so the patient will remember the assigned expiration/discard date of the drug.

The above described system can be provided in a kit that also contains sterile latex or non-latex gloves and 70% isopropyl alcohol pads for additional disinfecting of connector points and surfaces.

Additional safeguards and good techniques for compounding sterile products, such as those listed in the United States Pharmacopeia <797> guidelines, should be followed, where applicable, for added protection of the medication and the compounder i.e., wearing of a face mask.

Ultimately, a complete labeled, and ready-to-use bottle will be dispensed to the patient, for use and storage, by pharmacies, hospitals, clinics and other healthcare settings. In one embodiment, the bottle is an ophthalmic bottle.

In one embodiment, the disclosed system may be used for such medications as piperacillin-tazobactam, vancomycin, metronidazole, macrolide antibiotics, aztreonam, amphotericin B in conventional (desoxycholate) or liposomal forms, imipenem-cilastatin, ceftazidime, cefazolin, and other penicillins, cephalosporins or other related or non-related antimicrobial medications. Other medications that may be compounded using this system include antineoplastic/chemotherapeutic (5-fluorouracil, mitomycin, etc.) agents and other ophthalmic classes of medications. This system may be used together or without injectable medications such as those mentioned above as continuation of therapy post surgical or non surgical ophthalmic procedures. SEE TABLE 1 for the list of products that may be used with the system.

TABLE 1

Antibiotics

| Class | Generic/Brand |
|---|---|
| Lipopeptides | Daptomycin (Cubicin) |
| Fluoroquinolone | Gemifloxacin (Factive) |
| Lipoglycopeptides | Telavancin (Vibativ), 2009 |
| Cephalosporin (5th generation) | Ceftaroline (Teflaro), 2010 |
| Macrocyclics | Fidaxomicin (Dificid), 2011 |

| Generic | Brand Name |
|---|---|
| Aminoglycoside Antibiotics | |
| Amikacin | Amikin |
| Gentamicin | Garamycin, G-Mycin, Jenamicin |
| Kanamycin | Kantrex |
| Neomycin | Mycifradin, Myciguent |
| Netilmicin | Netromycin |
| Paromomycin | |
| Streptomycin | |
| Tobramycin | Nebcin |
| Cephalosporins | |
| First Generation | |
| Cefacetrile (cephacetrile) | Celospor, Celtol, Cristacef |
| Cefadroxil (cefadroxyl) | Duricef, Ultracef |
| Cefalexin (cephalexin) | Keflex, Keftab |
| Cefaloglycin (cephaloglycin) | Kefglycin |
| Cefalonium (cephalonium) | |
| Cefaloridine (cephaloradine) | |
| Cefalotin (cephalothin) | Keflin |
| Cefapirin (cephapirin) | Cefadyl |
| Cefatrizine | |
| Cefazaflur | |

TABLE 1-continued

| | |
|---|---|
| Cefazedone | |
| Cefazolin (cephazolin) | Ancef, Kefzol |
| Cefradine (cephradine) | Velosef |
| Cefroxadine | |
| Ceftezole | |
| Second Generation | |
| Cefaclor | Ceclor, Ceclor CD, Distaclor, Keflor, Ranicor |
| Cefamandole | Mandol |
| Cefmetazole | |
| Cefonicid | Monocid |
| Cefotetan | Cefotan |
| Cefoxitin | Mefoxin |
| Cefprozil (cefproxil) | Cefzil |
| Cefuroxime | Ceftin, Kefurox, Zinacef, Zinnat |
| Cefuzonam | |
| Third Generation | |
| Cefcapene | |
| Cefdaloxime | |
| Cefdinir | Omnicef, Cefdiel |
| Cefditoren | Spectracef |
| Cefetamet | |
| Cefixime | Suprax |
| Cefmenoxime | Cefmax |
| Cefodizime | |
| Cefotaxime | Claforan |
| Cefpimizole | |
| Cefpodoxime | Vantin |
| Cefteram | |
| Ceftibuten | Cedax |
| Ceftiofur | Excede |
| Ceftiolene | |
| Ceftizoxime | Cefizox |
| Ceftriaxone | Rocephin |
| Cefoperazone | Cefobid |
| Ceftazidime | Ceptaz, Fortum, Fortaz, Tazicef, Tazidime |
| Fourth Generation | |
| Cefclidine | |
| Cefepime | Maxipime |
| Cefluprenam | |
| Cefoselis | |
| Cefozopran | |
| Cefpirome | Cefrom |
| Cefquinome | |
| Not Classified | |
| Cefaclomezine | |
| Cefaloram | |
| Cefaparole | |
| Cefcanel | |
| Cefedrolor | |
| Cefempidone | |
| Cefetrizole | |
| Cefivitril | |
| Cefmatilen | |
| Cefmepidium | |
| Cefovecin | |
| Cefoxazole | |
| Cefrotil | |
| Cefsumide | |
| Cefuracetime | |
| Ceftioxide | |
| Carbapenems | |
| Imipenem, Imipenem/cilastatin | Primaxin |
| Doripenem | Doribax |
| Meropenem | Merrem |
| Ertapenem | Invanz |
| Quinolone Antibiotics | |
| First Generation | |
| Flumequine | Flubactin |
| Nalidixic acid | NegGam, Wintomylon |
| Oxolinic acid | Uroxin |
| Piromidic acid | Panacid |
| Pipemidic acid | Dolcol |

TABLE 1-continued

| | |
|---|---|
| Rosoxacin | Eradacil |
| *Second Generation* | |
| Ciprofloxacin | Cipro, Cipro XR, Ciprobay, Ciproxin |
| Enoxacin | Enroxil, Penetrex |
| Lomefloxacin | Maxaquin |
| Nadifloxacin | Acuatim, Nadoxin, Nadixa |
| Norfloxacin | Lexinor, Noroxin, Quinabic, Janacin |
| Ofloxacin | Floxin, Oxaldin, Tarivid |
| Pefloxacin | Peflacine |
| Rufloxacin | Uroflox |
| *Third Generation* | |
| Balofloxacin | Baloxin |
| Gatifloxacin | Tequin, Zymar |
| Grepafloxacin | Raxar |
| Levofloxacin | Cravit, Levaquin |
| Moxifloxacin | Avelox, Vigamox |
| Pazufloxacin | Pasil, Pazucross |
| Sparfloxacin | Zagam |
| Temafloxacin | Omniflox |
| Tosufloxacin | Ozex, Tosacin |
| *Fourth Generation* | |
| Besifloxacin | Besivance |
| Clinafloxacin | |
| Gemifloxacin | Factive |
| Sitafloxacin | Gracevit |
| Trovafloxacin | Trovan |
| Prulifloxacin | Quisnon |
| *Macrolide Antibiotics* | |
| Azithromycin | Zithromax |
| Erythromycin | |
| Clarithromycin | Biaxin |
| Dirithromycin | Dynabac |
| Roxithromycin | Rulid, Surlid |
| *Ketolides* | |
| Telithromycin | Ketek |
| *Penicillins* | |
| Amoxicillin | Amoxil, Polymox, Trimox, Wymox |
| Ampicillin | Omnipen, Polycillin, Polycillin-N, Principen, Totacillin |
| Bacampicillin | Spectrobid |
| Carbenicillin | Geocillin, Geopen |
| Cloxacillin | Cloxapen |
| Dicloxacillin | Dynapen, Dycill, Pathocil |
| Flucloxacillin | Flopen, Floxapen, Staphcillin |
| Mezlocillin | Mezlin |
| Nafcillin | Nafcil, Nallpen, Unipen |
| Oxacillin | Bactocill, Prostaphlin |
| Penicillin G | Bicillin L-A, Crysticillin 300 A.S., Pentids, Permapen, Pfizerpen, Pfizerpen-AS, Wycillin |
| Penicillin V | Beepen-VK, Betapen-VK, Ledercillin VK, V-Cillin K |
| Piperacillin | Pipracil |
| Pivampicillin | |
| Pivmecillinam | |
| Ticarcillin | Ticar |
| *Sulfonamides* | |
| Sulfamethizole | Thiosulfil Forte |
| Sulfamethoxazole | Gantanol, Urobak |
| Sulfisoxazole | Gantrisin |
| Trimethoprim- Sulfamethoxazole | Bactrim, Bactrim DS, Cotrim, Cotrim DS, Septra, Septra DS, Sulfatrim, Sulfatrim-DS |
| *Tetracycline Antibiotics* | |
| Demeclocycline | Declomycin |
| Doxycycline | Doryx, Vibramycin |
| Minocycline | Dynacin, Minocin, Monodox |
| Oxytetracycline | Terramycin |
| Tetracycline | Achromycin |
| *Glycylcyclines* | |
| Tigecycline | Tygacil |
| *Other Antibiotics* | |
| Vancomycin | Vancocin |
| Metronidazole | Flagyl, Helidac, Metizol, Metric 21, Neo-Metric, Noritate, Novonidazol |
| Tinidazole | Tindamax |
| Nitrofurantoin | Furadantin, Macrobid, Macrodantin |
| Chloramphenicol | Chloromycetin |
| *Oxazolidinones* | |
| Linezolid | Zyvox |
| *Rifamycins* | |
| Rifampin | Rifadin |
| Rifabutin | Mycobutin |
| Rifapentine | Priftin |
| *Lincosamides* | |
| Clindamycin | Cleocin |
| Lincomycin | Lincocin |
| *Streptogramins* | |
| Pristinamycin | Pyostacine |
| Quinupristin/dalfopristin | Synercid |

Fortified ophthalmic drops of cephalosporins, combination groups of antibiotics listed above, sodium sulfacetamide, acyclovir, cidofivir, ganciclovir, idoxuridine, trifluridine, amphotericin, clotrimazole, fluconazole, flucytosine, ketoconazole, miconazole, natamycin, voriconazole, Thiotepa, 5-fluorouracil mitomycin, paclitaxol, tetrahydonannabino marijuana (THC), cocaine, glycerin, hydroxyamphetamine, rose bengal solution, brilliant blue, indocyanine green (ICG) solution, albumin, autologous serum eye drops, cyclosporine with or without combination medications, methyl cellulose, tacrolimus, antioxidant/vitamin mixtures, acetazolamide, preservative-free eye drops which may include: include apraclonidine, betaxolol, bimatoprost, brimonidine, carbachol, clonidine, dipivefrin, dorzolamide, epinephrine, latanoprost, levobutanol, phospholine iodide, pilocarpine, pilocarpine combinations, travoprost, dexamethasone, methylprednisolone, prednisolonoe, rimexolone, triamcinolone, acetylcysteine, aminocaproic acid, bevacizumab, brilliant green, brilliant blue, dicofenac, ethylenediaminetetraacetic acid (EDTA), glutathione, interferon, polyhexamethylene biguanide (PHMB), physostigmine, povidone-iodine, silver nitrate, sodium chloride, sterile water or artificial tear combination product with or without methylcelluslose, tetrahydrolazine, vitamins, atropine, benoxinate, cylcopentolate, cyclopentolate combinations, cyclopentolate/phenylephrine, dapiprazole, homatropine, lidocaine, phenylephrine, proparacaine alone or in combination with other drugs, scopolamine, tetracaine, tropicamide, tropicamide combinations with cyclopentolate or phenylephrine, In another embodiment, the vented transfer device, with or without additional injection port may be sold as a part of a commercially available kit. These bottles can contain the vented transfer device, the bottle for mixing (which will be empty and not be provided with any powder or solution for mixing), with a twist on cap (which contains the special locking device), and the cap for closing the final compounded product. It can be made available as a retail product for retail pharmacy, the pharmaceutical market, or academic, institutional, research or public settings which require bottles for mixing eye products or non-eye products that requires protection of the product and the individual while mixing a powder to solution or a solution to solution in any setting. This system can also be considered for use in mixing other artistic, cosmetic, commercial or industrial products such as creams, gels, solutions, paints and glues.

According to one embodiment and referring to FIG. 1, a system for mixing compounds includes a first container 102 for containing a first compound 140. The first compound can be a drug in powder form. The first container 102 has a collar 132 that defines an opening into an interior of the container. A membrane 120 is disposed over the opening of the container 102. The membrane 120 is capable of being punctured in order to provide fluid communication to an interior of the container. The membrane 120 can be a metal foil, for example. A sleeve portion of the transfer device 100 is provided that is sized and shaped to removably engage the collar of the first container 102. The sleeve can include internal threads 130 that engage external threads 132 around the collar of the container as shown. A puncture member 124 is disposed on a first side of the sleeve. The puncture member sized and shaped to puncture the membrane in a first condition in which the sleeve is engaged with the collar (e.g., as the sleeve is threaded onto the collar, the puncture member is lowered relative to the membrane and advanced until the membrane is punctured. A luer lock fitting 128 is disposed on a second side of the transfer device 100 opposite the first side. The luer lock is sized and shaped to allow a syringe 106 to engage to the luer lock. The luer lock and the puncture member define a fluid communication passage such that fluid can be delivered through the luer lock and the puncture member and into the container when the sleeve is engaged to the collar. Accordingly, a syringe containing a second compound (e.g., a diluent fluid) can be engaged with the luer lock and the fluid in the syringe can be dispensed through the fluid communication passage and into the first container where it can mix with the first compound contained within the container.

A vent member 126 can be included that provides a fluid communication passage through a wall of the sleeve such that when the sleeve is in a first condition and engaged with the collar of the container air can be expelled from the container through the vent as fluid is introduced into the container through the luer lock. The vent can include a one-way valve that permits air in the container to be expelled and does not permit air to enter the container from the outside environment.

A protective cap 116 can also be included that is sized and shaped to be removably disposed over the membrane. The protective cap provides additional protect against inadvertent puncture of the membrane and being removable prior to engagement of the sleeve with the collar. The protective cap can be a removable plastic disk, for example.

After the sleeve is removed from the collar, a dropper tip 110 that is sized and shaped to be removably engaged to the collar such that the dropper tip can be attached to the first container. The dropper tip permits controlled dispensing of a mixture of the first compound and a fluid introduced into the first container through the luer lock. Referring to FIG. 4, the dropper tip can include a drain port that is disposed on an underside thereof. The drain port is sized and shaped to pass through the membrane when the dropper tip is engaged with the collar. The drain port provides a fluid communication passage through the drain port to a dispensing end of the dropper tip.

The system of FIG. 2 is similar to FIG. 1 but permits connection of a second container to the sleeve. The sleeve/transfer device 200 is a two-sided sleeve in that it includes threads for engagement of first and second containers 202, 204. The puncture member 210, 224 is also two sided in that it extends in both directions so that it can puncture the membranes of the first and second containers when the containers are engaged to the sleeve. The puncture member also defines two fluid passages, one to allow fluid transfer and one to provide equalization of pressure between the two containers as fluid is transferred. For example, as fluid is emptied from the second container into the first, are from the first container passes into the second. This prevents a vacuum from developing that would hinder transfer of fluid. In addition, a vent 216 is also provided to provide pressure equalization.

The system of FIG. 3 includes a sleeve that is integral with the second container. The sleeve is sized and shaped to removable engage with the collar of the first container. The collar of the second container is sized and shaped (e.g., tapered) such that it can puncture the membrane of the first container and enter into the collar of the first container.

The systems shown in FIGS. 1, 2, and 3 can be used to mix compounds of ceftazidime or vancomycin. For example, the first container can include vancomycin as the first compound and a diluting fluid can be added to the first container to mix into a medical treatment solution.

Directions for Use in a Specific Embodiment
1) In a clean and quiet area remove contents of kit and put on latex or non-latex containing compounding gloves. You may choose to also put on a surgical facial mask if available.
2) Remove bottle with drug powder (i.e. antibiotic) and remove the plastic cap and then the pressure sensitive aluminum security seal. Clean top with 70% isopropyl alcohol pad.
3) Remove the sterile vented transfer-connector from plastic wrapper and screw onto neck of ophthalmic bottle with powder until locked. This will break the inner membrane which maintains sterility of the inner chamber with powder.
4) Assemble the pre-filled syringe with diluent. Uncap syringe end and remove foil. Swab top with 70% isopropyl alcohol pad and then screw on/attach to the luer-lock top of the vented transfer-connector.
5) Slowly inject diluent into bottle powder vial and then (while still connected) swirl the contents of the mixture clockwise until the solution is clear or uniformly mixed in the case of suspensions. Do not shake. (view solution from clear side or bottom window panel). Once in solution/suspension unscrew the transfer-connector and syringe and discard.
6) Remove combined outer cap and Inner dropper tip from sterile plastic wrapping (without touching connection base to maintain sterility) and screw tip first and then cap onto the neck of the bottle until each lock into place. Ensure that both cap and dropper heads are tightened properly.
7) A Beyond-use Label with a discard after date is provided for the pharmacist or the physician to write the date in which the mixed solution or suspension will expire on and should be thrown out (see package insert for recommended expiration date).
8) In one embodiment, the bottle is an ophthalmic bottle.

Each kit to be commercially supplied as:
1) Bottle with drug as powder
2) Pre-filled syringe with diluent for mixing
3) Sterile vented transfer-connector
4) Sterile screw on dropper tip and sterile outer cap
5) Pads saturated with 70% isopropyl alcohol.
6) Beyond-use label with discard after date to be filled out and affixed after mixing.

7) Sterile latex or non-latex gloves for compounding.

8) In one embodiment, the bottle is an ophthalmic bottle.

This ready-to-mix and dispense medication compounding system provides: a pre-measured sterile diluent in a syringe that luer locks onto a sterile vented transfer device that twists on and connects onto a bottle with medication in a powder form for mixing, a primary and secondary sterility barrier found in the bottle, a unique drain spout, and a see through plastic window for viewing of the product while mixing. In one embodiment, this system also includes a unique threaded sterile dropper tip and cap. The sterile dropper tip contains a special lock-on dimple/nipple that will protect the dropper tip from opening and spilling of the drug solution or compromising the sterility of the solution once compounded and dispensed. In one embodiment, a traditional snap-on tip may also be used, however, the screw on is preferred for added security. The sterile dropper cap will then screw onto the dropper tip for easy closing and opening. Beyond-use stickers/labels are also provided to be used on the bottle so the patient will remember the expiration/discard date of the drug. Also provided is a kit comprising the disclosed system and contains sterile latex or non-latex gloves and 70% isopropyl alcohol pads to minimize the risk of extrinsic contamination of connector locations. Ultimately a complete, labeled, and ready-to-use bottle will be dispensed to the patient, for use and storage, by pharmacies, hospitals, clinics and other healthcare settings. The system may be used for compounding such medications as piperacillin-tazobactam, vancomycin, metronidazole, macrolide antibiotics, aztreonam, amphotericin B (in desoxycholate or liposomal formulations), imipenem-cilastatin, ceftazidime, cefazolin, and other penicillins, cephalosporins or other related or non-related antimicrobial medications. Other medications that may be compounded using this system include antineoplastic chemotherapeutic agents and other ophthalmic classes of medications. In specific embodiment, the system is for ophthalmic medication.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references cited herein are incorporated herein by reference in their entirety and for all purposes to the same extent as if each individual publication or patent or patent application was specifically and individually indicated to be incorporated by reference in its entirety for all purposes.

What is claimed is:

1. A method for sterilely mixing compounds to provide an ophthalmic compound for administration to an eye of a patient, the method comprising the steps of:

obtaining a first container, the first container containing a first compound, the first container having a collar defining an opening and a membrane disposed over the opening of the container, wherein the membrane is capable of being punctured in order to provide fluid communication to an interior of the container;

engaging a sleeve with the collar of the first container, the sleeve including a puncture member disposed on a first side of the sleeve and a luer lock disposed on a second side of the sleeve opposite the first side, the luer lock and the puncture member defining a fluid communication passage such that fluid can be delivered through the luer lock and the puncture member and into the container;

puncturing the membrane with the puncture member by engagement of the sleeve with the collar;

engaging a second container with the luer lock, the second container containing a fluid;

introducing the fluid into the first container through the luer lock and sleeve;

venting air from the first container through a vent member that provides a fluid communication passage through a wall of the sleeve as the fluid is introduced into the first container;

agitating the first container to create a mixture of the first compound and the fluid;

disengaging the second container and sleeve from the first container;

engaging a dropper tip with the collar, the dropper tip being sized and shaped to removably engage the collar and having a complementary structure to the sleeve such that the dropper tip can be attached to the first container with the sleeve removed from the first container, the dropper tip having a static open lumen and a drain port disposed on an underside of the dropper tip, the drain port being sized and shaped to pass through the membrane and provide a fluid communication passage through the drain port to a dispensing end of the dropper tip; and dispensing, in a controlled manner directly from the first container through the dropper tip to the patient eye, the mixture of the first compound and the fluid, wherein the first container is at least partially deformable to facilitate dispensing.

2. The method of claim 1, wherein the length of the vent is smaller than the diameter of the sleeve.

3. The method of claim 1, wherein a protective cap is disposed over the membrane, the protective cap providing additional protection against inadvertent puncture of the membrane, further including the step of removing the protective cap prior to engaging the sleeve with the collar.

4. The method of claim 1, wherein the second container is a syringe.

5. The method of claim 1, wherein the collar and the sleeve include threads that permit the removable engagement of the collar and sleeve.

6. The method of claim 1, wherein the vent includes a one-way valve that permits air in at least one of the first and second containers to be expelled and does not permit air, microbes and a combination thereof to enter at least one of the first and second containers from the outside environment.

7. The method of claim 1, wherein the fluid is a diluent for mixing with the first compound.

8. The method of claim 1, wherein the dropper tip includes a filter to prevent outflow of at least one of microbes, contaminants, unmixed drug and a combination thereof from the first container into a patient eye.

9. The system of claim 8, wherein the filter is a 5 micron filter.

10. The method of claim 1, wherein at least a portion of the first container is translucent such that contents of the first container can be viewed through the translucent portion.

11. The method of claim 1, wherein at least a first portion of the first container is opaque and at least a second portion is translucent such that contents of the first container can be viewed through the translucent portion.

12. The system of claim 1, wherein the dropper tip includes a locking mechanism to selectively, lockingly engage with the collar.

13. The system of claim 1, wherein the patient is a human or non-human animal.

14. A method for sterilely mixing compounds to provide an ophthalmic compound for administration to an eye of a patient, the method comprising the steps of:
- obtaining a first container, the first container containing a first compound, the first container having a collar defining an opening and a membrane disposed over the opening of the container, wherein the membrane is capable of being punctured in order to provide fluid communication to an interior of the container;
- engaging a sleeve with the collar of the first container, the sleeve including a puncture member disposed on a first side of the sleeve;
- puncturing the membrane with the puncture member by engagement of the sleeve with the collar,
- engaging a second container with the sleeve, the second container containing a fluid;
- introducing the fluid into the first container through the sleeve;
- venting air from the first container through a vent member that provides a fluid communication passage through a wall of the sleeve as the fluid is introduced into the first container;
- agitating the first container to create a mixture of the first compound and the fluid;
- disengaging the second container and sleeve from the first container;
- engaging a dropper tip with the collar, the dropper tip being sized and shaped to removably engage the collar and having a complementary structure to the sleeve such that the dropper tip can be attached to the first container with the sleeve removed from the first container, the dropper tip having a static open lumen and a drain port disposed on an underside of the dropper tip, the drain port being sized and shaped to pass through the membrane and provide a fluid communication passage through the drain port to a dispensing end of the dropper tip; and
- dispensing, in a controlled manner directly from the first container through the dropper tip to the patient eye, the mixture of the first compound and the fluid, wherein the first container is at least partially deformable to facilitate dispensing.

15. The method of claim 14, wherein the length of the vent is smaller than the diameter of the sleeve.

16. The method of claim 14, wherein a protective cap is disposed over the membrane, the protective cap providing additional protection against inadvertent puncture of the membrane, further including the step of removing the protective cap prior to engaging the sleeve with the collar.

17. The method of claim 14, wherein the second container is an ophthalmic bottle.

18. The method of claim 14, wherein the second container includes a collar defining an opening and a membrane disposed over the opening of the second container, and the sleeve includes a second puncture member, wherein the membrane of the second container is punctured by the second puncture member as a result of the engagement of the second container with the sleeve.

19. The method of claim 14, wherein the vent includes a one-way valve that permits air in at least one of the first and second containers to be expelled and does not permit air, microbes and a combination thereof to enter at least one of the first and second containers from the outside environment.

20. The system of claim 14, wherein the patient is a human or non-human animal.

21. The system of claim 14, wherein the dropper tip includes a locking mechanism to selectively, lockingly engage with the collar.

* * * * *